(12) United States Patent
Cohen-Armon et al.

(10) Patent No.: US 8,889,707 B2
(45) Date of Patent: Nov. 18, 2014

(54) TREATMENT OF ADDICTION

(71) Applicant: Malka Cohen-Armon, Tel Aviv (IL)

(72) Inventors: Malka Cohen-Armon, Tel Aviv (IL); Gal Yadid, Shoham (IL); Elad Lax, Netanya (IL)

(73) Assignee: Malka Cohen-Armon, Tel Aviv (IL)

( * ) Notice: Subject to any disclaimer, the term of this patent is extended or adjusted under 35 U.S.C. 154(b) by 0 days.

(21) Appl. No.: 13/761,761

(22) Filed: Feb. 7, 2013

(65) Prior Publication Data

US 2013/0203801 A1    Aug. 8, 2013

Related U.S. Application Data

(60) Provisional application No. 61/596,255, filed on Feb. 8, 2012.

(51) Int. Cl.
*A61K 31/473* (2006.01)
*C07D 221/12* (2006.01)
*A61K 45/06* (2006.01)

(52) U.S. Cl.
CPC .............. *A61K 31/473* (2013.01); *A61K 45/06* (2013.01)
USPC ............. 514/298; 546/79; 546/108; 514/279; 514/290

(58) Field of Classification Search
CPC ........................... A61K 31/473; C07D 221/12
USPC ............. 546/79, 101, 108; 514/279, 290, 298
See application file for complete search history.

(56) References Cited

U.S. PATENT DOCUMENTS

| | | | |
|---|---|---|---|
| 6,348,475 B1 * | 2/2002 | Zhang et al. .................. | 514/309 |
| 7,405,227 B2 * | 7/2008 | Kun et al. ..................... | 514/309 |
| 7,732,491 B2 * | 6/2010 | Sherman et al. .............. | 514/619 |
| 7,994,222 B2 * | 8/2011 | Ossovskaya et al. ......... | 514/617 |
| 8,377,985 B2 * | 2/2013 | Kun et al. ..................... | 514/457 |

OTHER PUBLICATIONS

Coren-Armon, Malka, et al. "Long-Term Memory Requires PolyADP-ribosylation" Science 2004. vol. 304. pp. 1820-1822.
Goldberg, Shmuel, et al. "PolyADP-ribosylation is required for long-term memory formation in mammals", Journal of Neurochemistry, 2009, pp. 1-8, International Society for Neurochemistry.
Schreiber, Valerie, et al. "Poly(ADP-ribose): novel functions for an old molecule", Nature Reviews Molecular Cell Biology, 2006, pp. 518-528, vol. 7.

\* cited by examiner

*Primary Examiner* — Golam M M Shameem
(74) *Attorney, Agent, or Firm* — Fleit Gibbons Gutman Bongini & Bianco PL; Martin Fleit; Paul D. Bianco (57) ABSTRACT

The invention discloses methods for preventing or treating addiction by administering to a subject in need thereof a PARP inhibitor.

15 Claims, 5 Drawing Sheets

TREATMENT OF ADDICTION

FIELD OF THE INVENTION

The invention disclosed herein generally concerns compositions and methods for prevention and treatment of addiction.

BACKGROUND

Addiction is a physical or psychological dependence on a substance or an activity that may be harmful to the addict or can interfere with the addict's normal life.

Many drugs, both illegal and legal, which may include prescription drugs, can cause a physical or psychological dependence. Illicit drug addiction has a negative impact on society as addicts tend to resort to crime to support their addiction. Examples of illegal addictive substances include: cocaine, marijuana, opiates, sedatives and amphetamines. Legal substances that can be addictive include caffeine, alcohol, nicotine, and some prescription medications.

Activities that can become addictive to the point that they interfere with the addict's normal life include: gambling, shopping, exercise, work, computer usage, internet usage, computer games, sex, cleaning and washing.

Cocaine is a commonly used, addictive, illicit drug, obtained from the leaves of the coca plant. Cocaine addiction is characterized by obsessive, compulsive drug consumption that is difficult to stop. Statistically, cocaine addicts that manage to stop their addiction exhibit a high rate of relapse as craving for cocaine remains after stopping use. In addicted users, abrupt stopping of cocaine usage can bring about withdrawal symptoms, such as paranoia, depression, sleep disturbances and anxiety. Cocaine addiction is commonly treated by psychotherapy in rehabilitation centers, but dropout rates in such programs are high. The withdrawal symptoms and the vulnerability to relapse make it difficult to succeed in providing a long-term cure for cocaine addiction.

In many addicts, cue reactivity is exhibited. Cue reactivity is a phenomenon in which an addict physiologically or psychologically responds to a stimulus related to his addiction. In many situations, exposure to a cue associated with an addict's past use of cocaine will elicit and/or increase craving in an addict. For example, for a person addicted to cigarette smoking or a person in a process of breaking an addiction to cigarette smoking, the smell of cigarette smoke or seeing another person light a cigarette may induce craving for a cigarette. For an alcoholic or alcoholic in rehabilitation, the sound of wine glasses clinking may induce a craving for alcohol. For a cocaine addict, seeing drug related paraphernalia may be a cue that induces craving. Cue reactivity may continue for long after the addictive behavior has stopped, increasing a risk that an addict may return to his or her addiction. Many rehabilitation programs encourage addicts to avoid "addiction" cues to facilitate their rehabilitation process.

The effect of polyADP-ribose-polymerase-1 (PARP-1) on long-term memory (LTP) in the sea slug Aplysia [1] and in mammals [2] has been demonstrated.

PUBLICATIONS

[1] Cohen-Armon et al. "Long-Term Memory Requires Poly-ADP-ribosylation" *Science* 2004, Vol 304, Pages 1820-1822.

[2] Goldberg S. et al. "PolyADP-ribosylation is required for long-term memory formation in mammals", *J. of Neurochemistry* 2009, Pages 1-8

[3] Schreiber, V, F Dantzer, J C Ame, and G. de Murcia. "Poly(ADP-ribose): novel functions for an old molecule." *Nat Rev Mol Cell Biol,* 2006: 517-28.

SUMMARY OF THE INVENTION

As demonstrated herein, the inventors of the invention disclosed in the present application have discovered that PARP inhibitors, e.g., PARP-1 inhibitors are efficient in treating a variety of additive behaviors and are additionally useful in suppressing relapse into addiction in subjects susceptible to regressing back to addictive state.

Thus, in a first aspect of the invention there is provided a method of treating or preventing an addictive behavior in a subject, said method comprising administering to said subject an effective amount of a Poly(ADP-ribose) polymerase (PARP) inhibitor or a composition comprising same.

In some embodiments, the PARP inhibitor is a PARP-1 inhibitor.

PARPs are a family of cell signaling enzymes which reside in cell nuclei. Poly-ADP-ribosylation is a fast, transient and energy consuming post-translational modification of nuclear proteins catalyzed by PARP enzymes. PolyADP-ribosylation of DNA-bound proteins evokes a transient relaxation of the highly condensed chromatin structure, rendering the DNA accessible to repair enzymes and to transcription factors. PARP-1, the most abundant nuclear PARP, is a highly conserved enzyme having a molecular weight of about 116 kDa which promotes chromatin modification and DNA transcription and repair [3].

The at least one PARP inhibitor employed in accordance with the invention is selected from N-(6-Oxo-5,6-dihydro-phenanthridin-2-yl)-(N,N-dimethylamino) acetamide, 4-iodo-3-nitrobenzamide, 4-[(3-[(4-cyclopropylcarbonyl)piperazin-4-yl]carbonyl)-4-fluoro-phenyl]methyl(2H)phthalazin-1-one, 8-Fluoro-2-(4-[(methylamino) methyl]phenyl)-1,3,4,5-tetrahydro-6H-azepino[5,4,3-cd]indol-6-one, (R)-2-(2-methyl pyrrolidin-2-yl)-1H-benzo[d]imidazole-4-carboxamide (ABT-888), 3-aminobenzamide and 2-(4-[(3S)-piperidin-3-yl]phenyl)-2H-indazole-7-carboxamide.

In some embodiments, the PARP inhibitor is a PARP-1 inhibitor, being for example N-(6-oxo-5,6-dihydrophenanthridin-2-yl)-(N,N-dimethylamino)acetamide (PJ-34).

The subject may be any animal, including a mammal, and particularly, a human.

In some embodiments, the addictive behavior is exhibited by said subject, following an unintentional or intentional exposure of said subject to at least one stimulus, trigger or cue, which induces in said subject an addictive behavior. In other words, the at least one stimulus may cause the subject to relapse into full or partial addiction to at least one agent or behavior.

In some embodiments, said subject to be treated in accordance with the invention has been previously reduced or eliminated use of the addictive agent or practice of the addictive or compulsive behavior in response to treatment with an effective amount of an anti-addiction treatment, and/or wherein the subject is no longer exposed to an effective amount of the anti-addiction treatment.

Thus, the invention also contemplates a method for preventing relapse into addiction. The method of the invention is also useful in reducing the addictive effect of re-exposure or continuous exposure to at least one agent, behavior or stimulus which induces the addictive behavior in an addicted subject or in a subject having a risk of developing an addiction. In some embodiments, the addiction is not induced by re-exposure or continuous exposure to at least one agent or behavior.

In another aspect, the invention provides a method of treating or preventing or reducing the probability of relapse to addiction, relapse use of an addictive agent or practice of an addictive or compulsive behavior in a subject, the method comprising administering to said subject in need thereof an effective amount of at least one PARP inhibitor.

In some embodiments, said subject to be treated has undergone a period of abstinence from, or reduced use of an addictive agent or behavior.

The invention similarly provides a method of preventing an addiction, the method comprising identifying a subject having a predisposition to addiction or who is at risk of developing an addiction; and providing to said subject an effective amount of PARP inhibitor. In accordance with this aspect of the invention, in order to determine a subject's state of being at risk of developing an addiction, or predisposition to addiction, the subject is first diagnosed by available diagnostic means, observation or analysis by a medical care provider. Predisposition factors may be genetic, biological/pharmacological and social factors.

As used herein, the term "treatment" or any lingual variation thereof refers to obtaining beneficial or desired results, including and preferably clinical results. The treatment according to the invention involves optionally either the reducing or amelioration of any one symptom or condition which is indicative or characteristic of addiction or relapse, or delaying the progression of such a symptom or condition. In some embodiments, the treatment results in withdrawal from addiction.

The treatment with said at least one PARP, e.g., PARP-1, inhibitor may be achieved by systemic administration, thereby said at least one PARP inhibitor passes the blood-brain barrier, and inhibits PARP in the central amygdala (CeA) region of the patient. In some embodiments of the invention, the PARP inhibitor is administered parenterally, for example, via intravenous administration. In some other embodiments, the PARP inhibitor is administered orally or internasally.

Similarly, the term "prevention" or any lingual variation thereof refers to arresting or delaying the onset or recurrence of a symptom or condition associated with addiction, or preventing the occurrence or recurrence of such symptoms.

The PARP inhibitor is typically administered in an amount effective to achieve a desired result of changing addiction-related behavior of the subject. The "effective amount" for purposes herein is determined by such considerations as may be known in the art. The amount must be effective to achieve the desired effect on addiction, depending, inter alia, on the type and severity of the addiction to be treated and the treatment regime. The "effective amount" or "therapeutically effective amount" is the amount effective to achieve the specified result of changing addiction-related behavior by a subject, the sufficient to affect a desired biological or psychological effect. As generally known, an effective amount depends on a variety of factors including the affinity of the PARP inhibitor to the ADP-ribose polymerase PARP, its distribution profile within the body, a variety of pharmacological parameters such as half life in the body, on undesired side effects, if any, on factors such as age and gender, etc. It should be emphasized, however, that the invention is not limited to any particular dose.

Generally speaking, addiction is defined as an uncontrolled and compulsive use (or abuse) of an agent or a behavioral pattern which is considered as an addictive behavior, even where the addictive behavior presents no harm to the subject practicing the behavior or to any other person associated with the subject. Within the scope of the present invention, the addictive behavior to be controlled, minimized or diminished (by way of treatment or prevention) may be of two types: physiological and psychological. Addictions in general often express both physical and psychological features.

In some embodiments, the addiction to be treated or prevented as disclosed herein is a physical dependence to an agent (an addictive agent) or to a particular behavioral pattern. The addiction expressing a physical dependence may be to an agent generally selected from illicit drugs, prescription drugs (and OTC drugs), alcohol or any combination thereof, which agent is referred to herein as the "addictive agent". Generally speaking, the agent causes a recurring compulsion by an individual to engage in use and abuse of the agent, despite harmful consequences to the individual's health, mental state or social life. The term "addictive behavior" similarly refers to a behavioral compulsion, such as gambling, and compulsive overeating, as further detailed hereinbelow.

In some embodiments, the addiction is caused by an addictive agent, being optionally selected amongst addictive recreational drugs and addictive medications.

In some embodiments, the addictive agent is selected from alcohol, caffeine, nicotine, cannabis and cannabis derivatives, opiates and morphine-like compounds, phencyclidine and phencyclidine-like compounds, sedative hypnotics, psychostimulants, amphetamines and amphetamine-related drugs.

In additional embodiments, the addictive agent is selected from alcohol, caffeine, nicotine, cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine.

In other embodiments, the addictive agent is selected amongst pain-killer such as alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol, tilidine and any combination of any of the aforementioned agents.

In yet additional embodiments, the addictive agent is selected from alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine and tramadol.

In some embodiments, the addiction is to cocaine.

In some embodiments, the addiction is in the form of a compulsive behavior (addictive behavior) and may be selected from obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising and overworking.

In some embodiments, the addiction is to two or more addictive agents and/or addictive behavior. In some embodiments, one or both of the addictions are to an addictive agent.

In some embodiments, the treatment or prevention of said addictive behavior is achieved by modulating PARP activity in the central amygdale of said subject. Thus, in another aspect, the invention provides a method of modulating the activity of PARP, e.g., PARP-1 in the central amygdale of a subject having an addictive behavior, to thereby affect treatment or prevention of addiction.

In some embodiments, the modulation of the activity of PARP is expressed in the central amygdala (CeA) region.

The amygdala is a heterogeneous structure located deep within the temporal lobe of the brain which is involved in many emotions and motivations. The amygdala is involved in the processing of emotions such as fear, anger and pleasure. The amygdala is also responsible for determining where and what memories are stored.

As known in the art, memory is the process by which information is encoded, stored, and retrieved and may be generally classified as long term memory (LTM) and short term memory (STM). Short-term memory allows recall of an event or information for a period of several seconds to a minute without rehearsal. The short-term memory generally has a strictly limited capacity and duration, which means that information, is not retained indefinitely. By contrast, long-term memory can store much larger quantities of information for potentially unlimited duration.

Memory consolidation is a category of processes that stabilize a memory trace after the initial acquisition. Reconsolidation is a category of processes in which previously consolidated memories can be made labile again through reactivation of the memory trace.

As such, the methods of the invention present the ability to use the PARP inhibitor as means to impair the subject's ability to retrieve a memory (or reconsolidation of a memory) of an addictive behavior even after or during unintentional or intentional exposure to a stimulus which otherwise would have caused reactivation of the memory and induce or strengthen the addictive behavior. Memories elicited by a variety of stimuli are reconsolidate after each episode of retrieval or reactivation, thereby allowing these memories to be updated, and disruption of this reconsolidation process by administering a PARP inhibitor results in a reduction in the motivational properties of stimuli associated previously with pleasure or aversive outcomes.

Thus, the invention also provides a method for affecting memory retrieval in a subject prone to relapse into addiction or for diminishing, suppressing or minimizing addictive behavior, the method comprising administering to said subject a PARP inhibitor prior, during or after intentional or unintentional exposure to a stimulus.

As used herein, the "stimulus" refers to a trigger or a cue which may be any material or any event captured by any one of a subject's senses (smells, visions, touch, etc), or any other factor (such as thoughts) which is capable of triggering, inciting, exerting or forcing a subject to express an addictive behavior. The stimulus, for example, may be re-exposure to an element of the addiction which is familiar to the subject and which exerts in said subject a feeling or a thought which may eventually lead to relapse or repeated behavior. For example, where addiction to alcohol is concerned, the stimulus may be the sight of another person consuming alcohol, or the mere odor of an alcoholic beverage. In another example, where the addiction is a compulsive behavior, such as gambling, the stimulus may be the subject's belief that he/she has the best chance of winning.

In addiction to drugs of abuse, the stimulus may be the subject's need to achieve a "high" or the subject's belief that by so doing survival of a stressful event may be the only way to overcome.

In some embodiments, the stimulus causing reinstatement of drug abuse or of a compulsive behavior is one or more of stress, re-exposure to a drug or drug-priming, and environmental triggers or cues.

In some embodiments, the treating or prevention an addictive behavior is achievable by modulating long-term memory. In some embodiments, the modulation of long-term memory is by interfering with a PARP1-Erk2 dependent mechanism. In further embodiments, the interfering with the said mechanism is by modulating the regulation of immediate early gene expression implicated in long-term memory. In further embodiment said modulating is achieved by down-regulating immediate early gene expression implicated in long-term memory.

The invention further contemplates uses and compositions comprising at least one PARP inhibitor for treating or prevention an addictive behavior in a subject.

The compositions employed by the methods of the invention may include pharmaceutically acceptable carriers as described herein, for example, vehicles, adjuvants, excipients, or diluents, which are well-known to those who are skilled in the art and which are readily available to the public. It is preferred that the pharmaceutically acceptable carrier be one which is chemically inert to the PARP inhibitors and one which has no detrimental side effects or toxicity under the conditions of use.

The choice of carrier will be determined in part by the particular PARP inhibitor, as well as by the particular method used to administer the composition. Accordingly, there is a wide variety of suitable formulations of the pharmaceutical composition employed in accordance with the invention. The following formulations for oral, aerosol, parenteral, subcutaneous, intravenous, intramuscular and interperitoneal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the PARP inhibitor, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the PARP inhibitor in a flavor, usually sucrose and acacia or tragacanth, as well as pastilles comprising the PARP inhibitor in an inert base, such as gelatin and glycerin, or sucrose and acacia, emulsions, gels, and the like containing, in addition to the PARP inhibitor, such carriers as are known in the art.

The PARP inhibitor employed in accordance with the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The PARP inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations typically contain from about 0.5 to about 25% by weight of the PARP inhibitor in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use.

The PARP inhibitor may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

In the compositions used in accordance with method of the invention, the PARP inhibitor may be used as its pharmaceutically acceptable acid addition salt. These salts include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. The salts of may similarly be of amino acids such as arginate and the like and gluconate, galacruronate.

The acid addition salts of any of the basic PARP inhibitor may be prepared by contacting the free base form with a sufficient amount of a desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," J. of Pharmaceutical Science, 66:1-19 (1977)).

The base addition salts of any acidic PARP inhibitor may be prepared by contacting the free acid form with a sufficient amount of a desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The invention also provides kits and commercial packages comprising a PARP inhibitor and instructions for use.

BRIEF DESCRIPTION OF DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF THE INVENTION

A protocol for the treatment of addiction has been tested in mammals and has proven to be effective in treatment of addiction. Details of a protocol and experimental results showing its success are depicted below.

Figure 1:
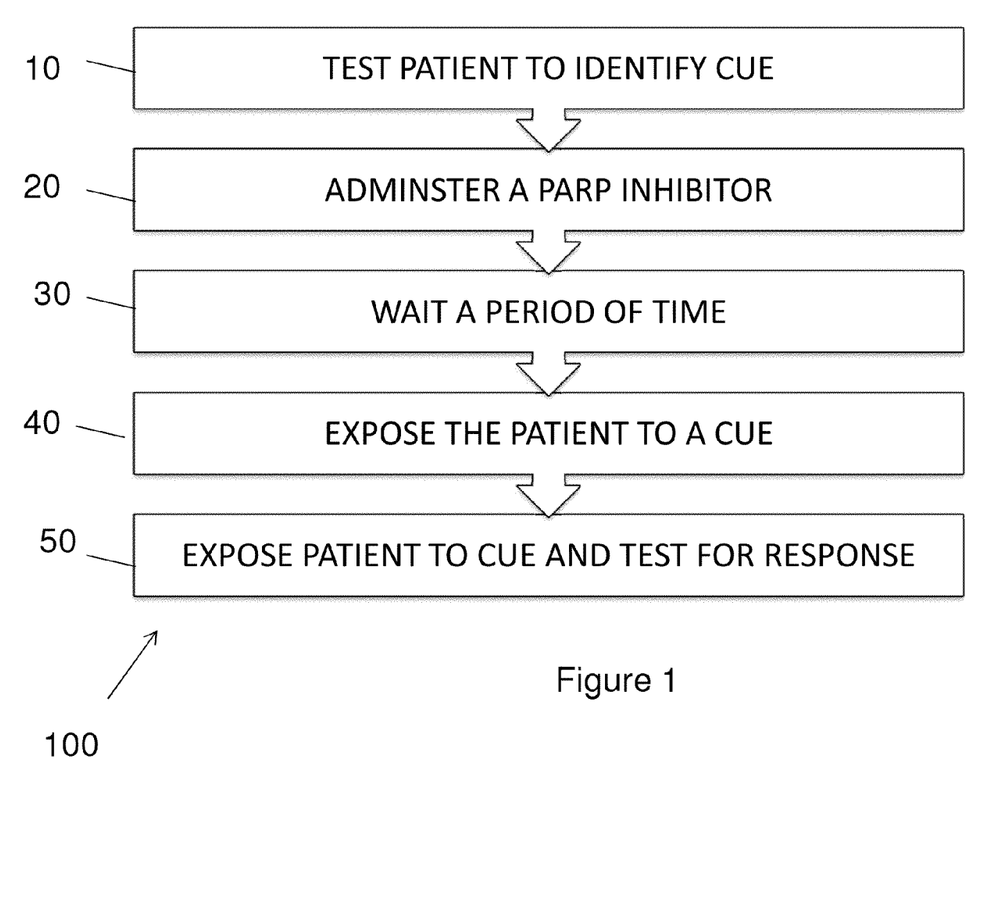
FIG. 1 shows a flow-diagram depicting a protocol according to an embodiment of the invention, for treatment of cocaine addiction using a PARP-1 inhibitor.

FIG. 1 shows a flow diagram of a protocol (protocol 100) for treatment of addiction. The protocol comprises block 10, testing a patient to identify a cue; block 20, administering a PARP inhibitor; block 30, waiting a period of time; block 40, exposing the patient to a cue; and block 50, exposing the patient to a cue and testing for a response.

An embodiment of the invention relates to a method of treatment of an addiction according to protocol 100 in FIG. 1. Embodiments of the invention relate to methods of treatment of addiction according to parts of protocol 100.

Block 10 comprises testing a patient addicted to a substance to identify a cue associated with the patient's addiction. A variety of cues can trigger craving in an addict. An examination of the patient can be performed by exposing the patient to a variety of suspected visual, audio or olfactory cues and observing the patient's changes in physiological parameters in response to suspected cues. In an embodiment, the physiological parameter is heart rate or skin conductance. In an embodiment of the invention, the patient is exposed to a variety of suspected visual, audio or olfactory cues and is asked to respond to questions regarding the intensity of craving experienced in response to each of the suspected cues. In an embodiment, the audio cue is a musical cue.

In block 20 a PARP-1 inhibitor is administered to the addicted patient. In some embodiments of the invention, the PARP inhibitor is a PARP-1 inhibitor. In an embodiment, the PARP inhibitor is selected from the group of inhibitors or a pharmaceutically acceptable salts thereof: N-(6-Oxo-5,6-dihydrophenanthridin-2-yl)-(N,N-dimethylamino)acetamide, 4-iodo-3-nitrobenzamide, 4-[(3-[(4-cyclopropylcarbonyl)piperazin-4-yl]carbonyl)-4-fluorophenyl]methyl(2H)phthalazin-1-one, 8-Fluoro-2-(4-[(methylamino)methyl]phenyl)-1,3,4,5-tetrahydro-6H-azepino[5,4,3-cd]indol-6-one, (R)-2-(2-methylpyrrolidin-2-yl)-1H-benzo[d]imidazole-4-carboxamide, 3-aminobenz amide and 2-(4-[(3S)-piperidin-3-yl]phenyl)-2H-indazole-7-carboxamide.

In some embodiments of the invention, the PARP inhibitor is administered to a region of the brain in which PARP activity is increased. In some embodiments, the region of the brain is the CeA. In some embodiments, the PARP inhibitor is administered systemically, passes the blood-brain barrier, and inhibits PARP in the CeA of the patient. In other embodiments of the invention, the PARP inhibitor is administered parenterally, for example, via intravenous administration. In some embodiments, the PARP inhibitor is administered orally. In some other embodiments, the PARP inhibitor is administered via intranasal administration.

In some embodiments of the invention, the dose is sufficient to inhibit PARP activity in the CeA of the patient. In some embodiments of the invention, the daily dose of PARP inhibitor is between 0.01 mg/kg (milligrams per kilogram) and 10 mg/kg.

Block 30 comprises waiting a period of time after the administration of the PARP inhibitor of block 20. In an embodiment, the time is less than 24 hours. In an embodiment, the time waited is less than 2 hours. In an embodiment, the time waited is less than 1 hour. In an embodiment, the time waited is 0 minutes.

Block 40 comprises exposing the patient to a cue associated with the patient's addictive behavior.

Block 50 comprises exposing the patient to a cue associated with the patient's addiction and testing to determine if a same physiological response or the same intensity of craving is experienced as in block 10. If there is a change in physiological response indicative of craving in block 50 relative to block 10, such as a lowering in physiological response or lowering of intensity of craving, this indicates that the treatment protocol 100 is successful in reducing the patient's craving and in treating the patient's addiction.

If the treatment according to protocol 100 is not successful, treatment can be repeated, for example, by repeating the protocol according to blocks 10, 20, 30, 40 and 50, or any combination thereof. In repeating the protocol, alternative cues can be used according to block 40 and/or dosage of administration according to block 20 can be modified. If treatment according to protocol 100 is successful in reducing the patient's craving, the patient may be subsequently subjected to retesting for effect according to block 50.

In some embodiments of the invention, protocol 100 is repeated. In some embodiments, the protocol is repeated a week after the first administration. In some embodiments, the protocol is repeated a month, 6 months or a year after the first administration.

In order to determine if protocol 100 would be effective in humans, a rat model was performed. The model was initiated by causing addiction to cocaine and by causing the rats to associate cocaine addiction with being in a specific compartment (i.e. a specific cage that the rats were placed in) that acted as a cue. The addicted rats were then administered a PARP inhibitor as in block 20 and then after a period of time, as in block 30, were allowed access to the cocaine-associated compartment as in block 40. Subsequently, upon exposing the rats to the cue as in block 50, the craving for cocaine was lowered, as expressed by the rats' tendency to spend less time in the cocaine-associated compartment.

As seen in the rat model, it is suggested that in humans, protocol 100 can be effective in lowering craving, decreasing relapse, and treating addiction.

Example 1

Conditioning of Rats for Place Preference

Male Sprague-Dawley rats weighing 250-300 g (grams) were maintained under conditions of constant temperature (23° C.) and humidity (50%) in a reverse 12:12 hrs (hours) light/dark cycle, with free access to food and water. In order to determine rats' response to cocaine related cues, a Conditioned Place Preference (CPP) apparatus was used. The CPP apparatus consisted of a 30-cm-(centimeter) high white plastic box, 22×90 cm, divided into two compartments (22×40 cm each) that were separated by two 30-cm-high dividers, creating a narrower, 10-cm-wide section. The two compartments differed; one having black and white striped walls and the other having walls with stripes in different shades of gray. Both compartments had equally spaced perforations on the floor. The middle section was neutral in color, with white walls. A counterbalanced protocol was used for training and testing of rats. For baseline measurements on day 1, each rat was individually placed in the middle section of the CPP apparatus. The gates between the compartments were then opened, allowing the rats free access to all three zones for 30 min. The amount of time spent in each of the three zones was recorded. On training days (days 2-11), the experimental (cocaine-conditioned) group of rats was injected with cocaine (15 mg/kg) every other day and with an equivalent volume of saline on the alternate days. Immediately after each injection, rats were accordingly placed in the cocaine-associated (gray-walled) compartment, or in the saline-associated compartment (striped walls) for 20 min (minutes). Control (saline-treated) rats received daily injections of saline only, and were alternately placed in one of the two compartments. During training sessions, the dividers between each compartment and the adjacent section were closed.

For testing of cue-associated memory retrieval on day 12, rats were again allowed free access to all three zones for 15 min, and the amount of time spent in each was recorded. Between all trials the apparatus was thoroughly cleaned with 70% ethanol and wipes, and turned by 180 degrees to control for any possible confounding effects, such as amount of light. The behavior of the rat during each test was recorded on a computer-based event recorder. EthoVision 3.1 (Noldus Information Technology) was used for off-line analysis.

Figure 2A:
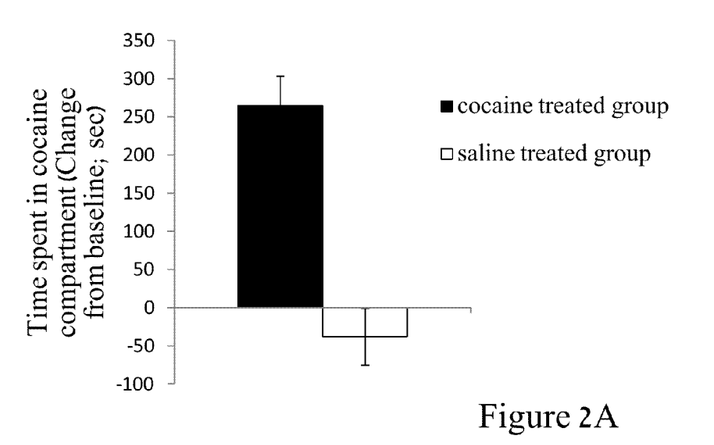
FIG. 2A shows a histogram comparing preference of addicted rats versus non-addicted rats to remain in a cocaine-associated region of a cage (compartment).

Two groups of rats, a cocaine-conditioned group and a control group, were conditioned for CPP as described. Ten rats were in each group. Pre-conditioning baseline CPP measurements showed no difference between prospective experimental and control groups in preference for either of the CPP compartments. In the testing of memory retrieval, cocaine-conditioned rats spent a significantly longer amount of time in the cocaine-associated compartment, as compared to controls (*$p<0.0005$, t-test), as can be seen in FIG. 2A.

During the training phase of the CPP model, the cocaine-addicted rats associate drug administration with a specific compartment, indicating that presence in that compartment signifies a drug-related cue. During testing, cocaine-addicted rats enter the cocaine-associated compartment, are "triggered" by the associated cue, and remain more time than the control rats in that compartment because of their craving of cocaine.

Example 2A

Impact on Cocaine Administration and Subsequent Memory Retrieval on PARP-1 Activation in the Brain Immediately after completion of the CPP memory retrieval testing, cell nuclei from various memory-related regions such as the CeA, BLA (basolateral amygdala), dentate gyms, striatum, hippocampal cornu ammonis area 3, prefrontal cortex and accumbens nucleus, were isolated for measurement of PARP-1 activation in the cells' nuclei. PARP-1 activation was assayed by immunolabeling of polyADP-ribose polymers formed mainly on activated PARP-1.

Brain punches were taken from the dentate gyms, striatum, hippocampal cornu-ammonis area, prefrontal cortex, arcuate nucleus, CeA and BLA, from three rats in each group. For extraction of cell nuclei, specific brain tissues were first treated (5-min on ice) with lysis buffer (pH-7.5) containing 0.2% NP-40, 1 mM DTT, 0.1 EDTA, 10 mM KCl, 1.5 mM $MgCl_2$, 1% protease inhibitors (Sigma), and 20 mM Tris-HCl. The lysates were then centrifuged (6,000-rpm, 5-min, 4° C.), and nuclear proteins were extracted from the pellets by treatment (30-min on ice) with extraction buffer (pH-7.5) containing 0.55 mM NaCl, 0.1 EDTA, 1.5 mM $MgCl_2$, 20% glycerol, 1 mM DTT, 1% protease inhibitors, and 10 mM Tris-HCl. The supernatants obtained after further centrifugation (15,000-rpm for 15-min at 4° C.) contained extracted nuclear proteins, which were size-separated by polyacrylamide-gel electrophoresis (PAGE), and identified after electrotransfer to nitrocellulose membranes (Western blot technique). Total PARP-1 and polyADP-ribosylated PARP-1 were identified on the nitrocellulose membrane by double immunolabeling with a monoclonal anti-ADP-ribose polymer antibody (Anti-PAR LP98-10; Alexis, Lausanne, Switzerland) and a polyclonal anti-PARP-1 antibody (MC1522; Serotec Oxford, UK) Immunolabeled PARP-1 was also used as the loading control. Activation of PARP-1 was measured by the level of its polyADP-ribosylation and was presented in terms of normalized molar ratio of polyADP-ribosylated PARP-1 (PAR) relative to total PARP-1 protein.

Figure 2B:
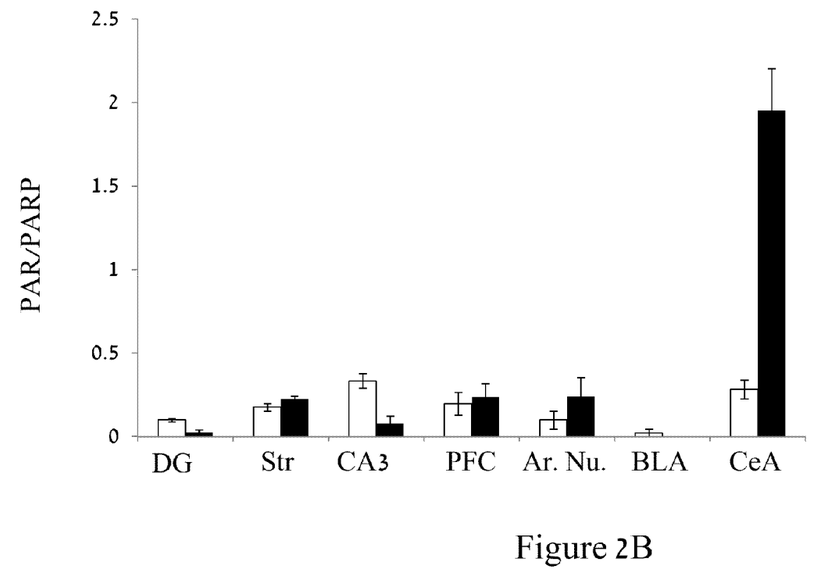
FIG. 2B shows a histogram of a ratio of PAR/PARP (ADP-ribose polymers/polyADP-ribose polymerase) which is representative of PARP-1 activation in various parts of rat brain of addicted rats immediately following presence in a cocaine-associated compartment (ADP-ribosylation of PARP-1 comprises more than 95% of the measured poly-ADP-ribosylation in the nucleus).

Significantly pronounced polyADP-ribosylation in the CeA of cocaine-conditioned rats, as compared to the BLA of the cocaine-conditioned rats and to all other brain tissues examined in cocaine-conditioned and control rats was found (p<0.001; FIG. 2B), indicating increased PARP activity in cocaine-addicted rats immediately following memory retrieval testing.

Example 2B

Figure 3A:
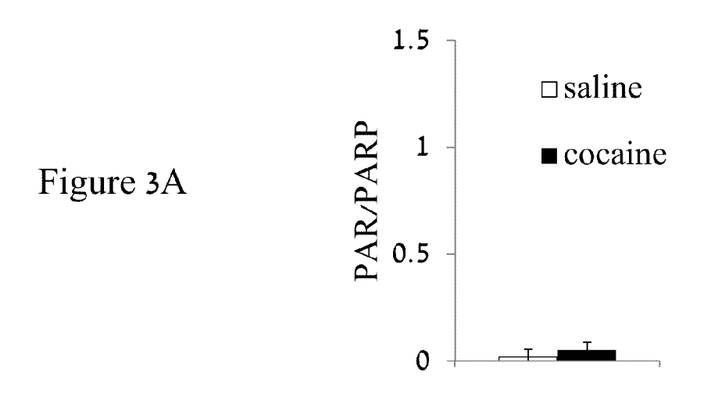
FIG. 3A shows a histogram of a ratio of PAR/PARP-1, which is representative of PARP activation in the central amygdala (CeA) region of cocaine-addicted rat brains following addiction, without subsequent exposure to a cocaine-associated compartment.

Determination of the Effect of CPP without Memory Retrieval Testing on PARP-1 Activation In order to determine that the observed increase in PARP-1 activation in Example 2A was attributed to contextual memory retrieval, rather than to consolidation, that is to a gradual stabilization of cocaine-conditioned memory throughout the training process, rats were subjected to 10-day cocaine- or saline-CPP training, but not to the subsequent memory retrieval test. 6 rats were tested in each group. Levels of polyADP-ribosylation were determined as in Example 2A. The levels measured in the CeA of cocaine-CPP rats after training were similar to controls (p>0.05; FIG. 3A).

Example 2C

Figure 3B:
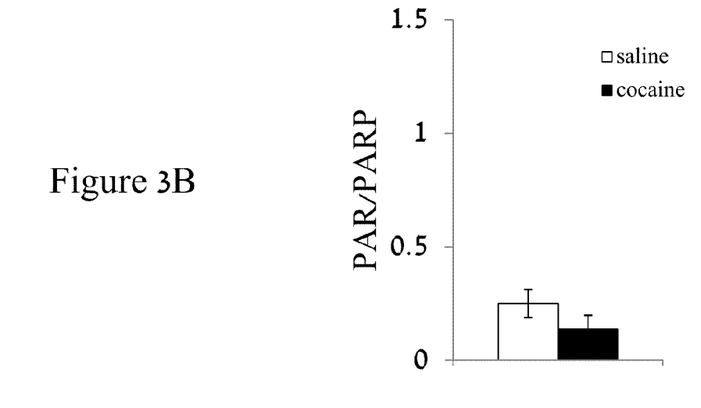
FIG. 3B shows a histogram of a ratio of PAR/PARP-1 representative of PARP activation in the CeA after acute cocaine administration without subsequent exposure to a cocaine-associated compartment.

Determination of the Effect of Acute Cocaine Administration without Memory Retrieval Testing on PARP-1 Activation Naive rats (3 per group) administered an acute intraperitoneal (i.p.) injection of either cocaine (15 mg/kg) or saline were tested for PARP activation. CeA polyADP-ribosylation levels of PARP-1 were determined as in Example 2A. The levels measured one hour after the acute injection showed no difference between the groups (p>0.05; FIG. 3B). In summary, examples 2A-C show that rats expressing cocaine-CPP demonstrated significant PARP-1 activation in the CeA but not in the adjacent BLA or other memory-related regions. Because PARP-1 activation was not found in rats subjected to cocaine conditioning alone, it is evident that the activation of PARP-1 can be attributed to memory retrieval, and not to the process of memory consolidation.

Example 3A

Inhibition of PARP-1 Activity and its Effect on Cocaine-Associated Memory Retrieval To further assess the involvement of PARP-1 activation in retrieval of cocaine-associated contextual memory, effect of a potent PARP inhibitor, PJ-34, (N-(6-Oxo-5,6-dihydro-phenanthridin-2-yl)-(N,N-dimethylamino)acetamide hydrochloride, (obtained from Alexis, Lausanne, Switzerland) on cocaine-CPP expression was determined Rats were split into three groups, each group having 6 rats. Rats were anesthetized with ketamine-hydrochloride (100-mg/kg) and xylazine (10-mg/kg; i.p.). A guide cannula (30 gauge) was implanted 1-mm (millimeter) above the CeA (two groups of rats) or the BLA (one group), sealed with a cannula dummy (Plastics One), and secured to the skull with screws and dental acrylic cement. Coordinates of the cannula relative to Bregma (Paxinos 2005) were as follows: CeA: anterior −2.56, lateral −4, ventral −8 mm; BLA, anterior −2.8, lateral −5, ventral −8.5 mm. Rimadyl (2-mg/kg) was injected (i.p.) after surgery. Canula was implanted unilaterally in the right hemisphere in order to avoid side effects. Rats were allowed to recover from surgery for 5-7 days before undergoing CPP training and testing.

All animals were then trained for cocaine-CPP for 10 days. Rats subsequently received an intra-CeA infusion of either PJ-34 or vehicle, or an intra-BLA infusion of PJ-34.

The infusion was prepared by adding PJ-34 at a concentration of 50 microM (micromolar) to an artificial cerebrospinal fluid (aCSF) vehicle (pH 7.4) consisting of 126 mM NaCl, 2.4 mM $CaCl_2$, 1.2 mM KCl, 1.2 mM $MgCl_2$, 1.2 mM $NaH_2PO_4$, and $NaHCO$. Thirty min before CPP testing, the solution (total volume 1.2 microl (microliter)) was infused via the guide cannula, by means of an electronic syringe pump (CMA 400, CMA/Microdialysis). Control rats received similar infusions of vehicle only (1.2 microl). The internal cannula remained in place for 5 min after the infusion, to avoid reflux.

Figure 4A:
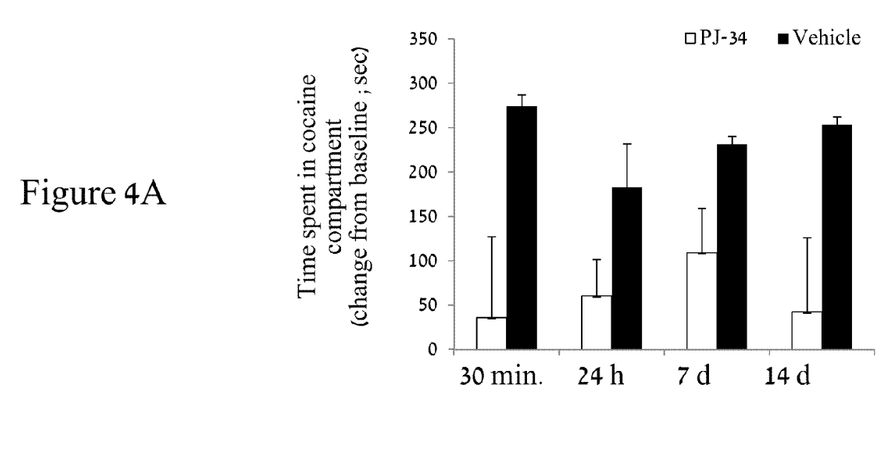
FIG. 4A shows a histogram of time spent in a cocaine-associated compartment in cocaine-addicted rats administered a PARP-1 inhibitor versus control rats administered saline before exposure to a cocaine-associated compartment.

Post-conditioning memory retrieval was examined 30 min after infusions. Preference for the cocaine compartment was abolished in intra-CeA PJ-34-infused rats, as opposed to intra-CeA vehicle-infused and intra-BLA PJ-34-infused rats (p<0.01; FIG. 4A). This effect persisted in post-conditioning tests conducted 24 hours later, 7 days later and 14 days later (p<0.01; FIG. 4A).

Example 3B

Inhibition of PARP-1 Activity and its Effect on Memory Reconsolidation

Figure 4B:
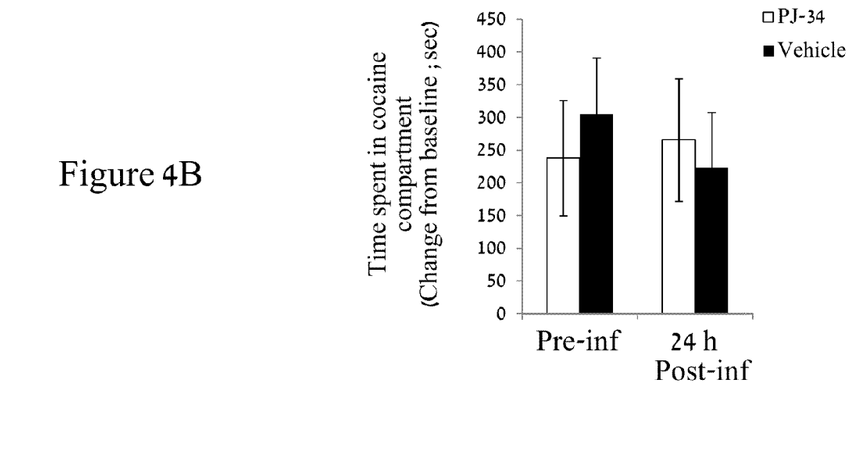
FIG. 4B shows a histogram of time spent in a cocaine-associated compartment in cocaine-addicted rats administered a PARP-1 inhibitor versus control rats administered saline after exposure to a cocaine-associated compartment.

Reconsolidation is a process in which memories, upon their retrieval, enter a transient state wherein they might become prone to change, for example, by external application of various inhibitors. An effect of acute PARP-1 inhibition on reconsolidation of memory for the cocaine-associated environment was tested by implanting in two groups of rats a guide cannula in the CeA and subjecting them to 10 days of cocaine-CPP training, as described in the above example. Subsequent testing of cocaine-CPP memory retrieval was immediately (within <1 min) followed by infusion of either PJ-34 or vehicle. Memory retrieval was tested again 24 hrs later. In contrast to Example 3A in which a PARP inhibitor was administered before memory retrieval testing, in this example expression of cocaine-CPP was similar in both groups on both test days (p>0.05; FIG. 4B).

Example 3C

Figure 5A:
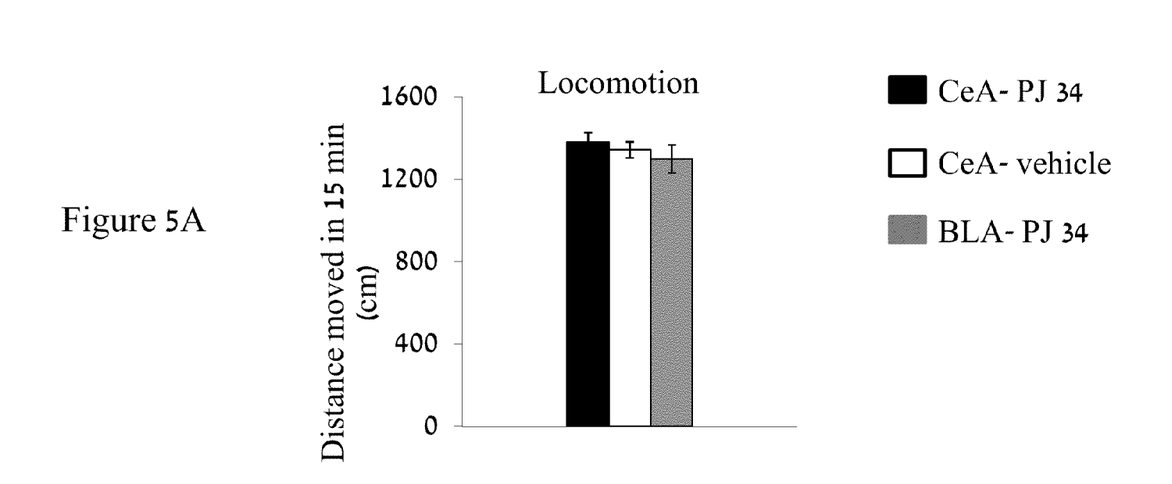
FIGS. 5A and 5B show histograms showing locomotion (FIG. 5A) and object recognition (FIG. 5B) in cocaine addicted rats administered with PARP-1 inhibitors versus rats administered with vehicle (artificial cerebro-spinal fluid, CSF).

Determination of the Effect of PARP-1 Activity on Locomotion and on Non-Cocaine Associated Memory Locomotor activity and newly formed short-term and long-term memory were tested in all three groups described in example 3A immediately after the first memory retrieval test. Locomotor activity was tested by placing rats in an open field (60×60 cm) apparatus with 30-cm-high walls. Following 10 min habituation, their locomotor activity in the open field was measured during the 15 min testing period. FIG. 5A shows average distance traveled for each group in the open field. No significant difference between the three groups was detected, as shown in FIG. 5A. In order to test short term and long term memory, an object recognition test was used. Rats were placed in the open field apparatus after memory retrieval testing described in example 3A. Four objects (A1, A2, B and C), similar in texture, color patterning and size (8 cm long and 8 cm high) but with distinctive shapes, were used. The training session was conducted 1 hr after a 10 min habituation to the arena. Each rat was placed for 5 min in the open field with two identical objects (A1 and A2) positioned in two adjacent corners, 10-cm from the walls. Short-term memory was assessed 1.5 hrs after the training session by analysis of the rat's exploration of the open field for 5 min in the presence of one familiar (A) and one novel object (B). "Exploration" was defined as sniffing or touching the object with the nose and/or forepaws.

The exploratory preference for each object was calculated as the time (t) spent in exploring that object expressed as the percentage of total exploration time $[(t_{A2}/(t_{A1}+t_{A2})\times 100]$. Short-term memory (STM) recognition was evaluated as the time spent by the rat in exploring the novel object (B), expressed as a percentage of the total exploration time $[STM=(t_B/(t_{A1}+t_B)\times 100]$. Between trials the objects were washed with 10% ethanol solution. For the long-term memory (LTM) test conducted 24 hrs after the training session, the same rat was allowed to explore the field for 5 min in the presence of the same familiar object (A) and a novel object (C). LTM recognition was evaluated as $(t_C/(t_{A1}+t_C)\times 100$. Rats were removed from the open field back to their home cage upon termination of each trial.

Figure 5B:
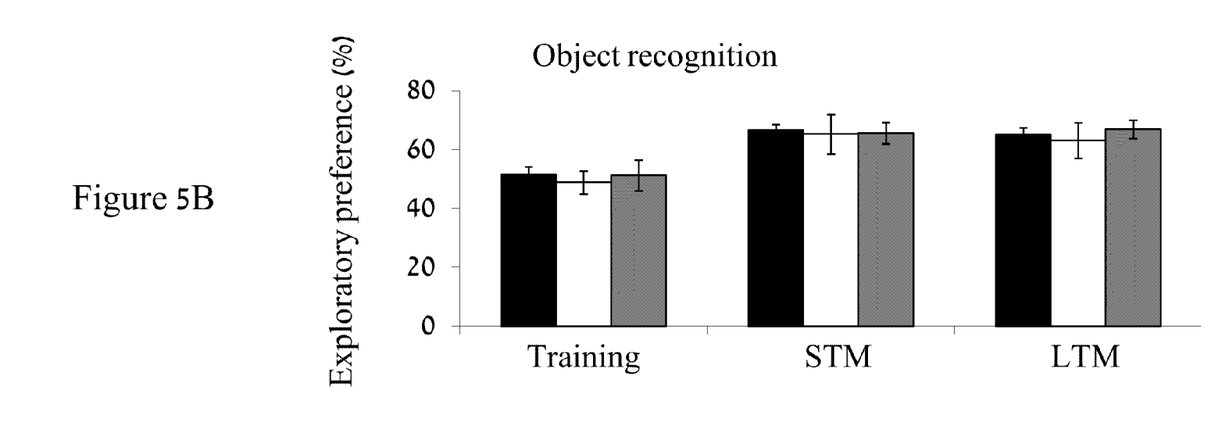

The object recognition tests showed no significant differences between the three groups (p>0.05; FIG. 5B). These findings indicate a selective effect of PARP-1 inhibitors on retrieval of drug-associated memory, while other earned memories are left intact.

In summary of examples 3A and 3B, pharmacological inhibition of PARP-1 in the CeA prior to cocaine-CPP testing showed long-lasting disruption of memories associated with the previous environmental preference of rats. This effect was not caused by a non-specific interference in physical performance or general memory, as evident by the fact that PARP-1 inhibition did not impact locomotion or STM or LTM. Therefore, it is evident that PARP-1 inhibition selectively blocks retrieval of cocaine-associated contextual memory without impairing the ability to retrieve other memories.

Inhibition of PARP-1 after memories for cocaine-associated cues had already been retrieved did not affect cocaine-CPP expression. This indicates that polyADP-ribosylation involved in cocaine-CPP expression is a fast and transient event, which is specific to cocaine-associated memory retrieval, and not linked with reconsolidation of these memories.

It has been shown in cocaine-addicted rats that reward-related cues are accompanied by an activation of PARP in the CeA, and that inhibition of PARP-1 in the CeA by administration of a PARP-1 inhibitor can eliminate the association between the cue and the rewarding addictive behavior, even long after the PARP-1 inhibitor was administrated. Similarly, in patients suffering from addictive behaviors, associations between cues which patients associated their awards can be eliminated by inhibiting PARP activation in the CeA. This effect can have a long term influence on the patient and prevent the patient from relapsing to the addiction long after the administration of a PARP inhibitor.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method of treating an addictive behavior in a subject, said method comprising administering to said subject an effective amount of a Poly(ADP-ribose) polymerase-1 (PARP-1) inhibitor or a composition comprising same.

2. The method according to claim 1, wherein the addictive behavior is exhibited by said subject, following exposure of said subject to at least one stimulus, which induces in said subject an addictive behavior.

3. The method according to claim 1, wherein the addiction is a physical dependence to an addictive agent or to an addictive behavior.

4. The method according to claim 3, wherein said addictive agent is selected from the group consisting of addictive recreational drugs and addictive medications.

5. The method according to claim 3, wherein said addictive agent is selected from the group consisting of alcohol, caffeine, nicotine, cannabis and cannabis derivatives, opiates and morphine-like compounds, phencyclidine and phencyclidine-like compounds, sedative hypnotics, psychostimulants, amphetamines and amphetamine-related drugs.

6. The method according to claim 3, wherein said addictive agent is selected from the group consisting of alcohol, caffeine, nicotine, cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine.

7. The method according to claim 6, wherein said addictive agent is cocaine.

8. The method according to claim 3, wherein said addictive agent is a pain-killer or a combination of pain-killers.

9. The method according to claim 8, wherein said pain-killer is selected from the group consisting of alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol and tilidine.

10. The method according to claim 3, wherein said addictive agent is selected from the group consisting of alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine and tramadol.

11. The method according to claim 3, wherein said addictive behavior is selected from the group consisting of obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising and overworking.

12. The method according to claim 3, wherein said addiction is to more than one of an addictive agent and/or addictive behavior.

13. The method according to claim 1, wherein the PARP-1 inhibitor is N-(6-oxo-5,6-dihydrophenanthridin-2-yl)-(N,N-dimethylamino)acetamide (PJ-34) or 2-[(R)-2-methylpyrrolidin-2-yl]-1H-benzimidazole-4-carboxamide (ABT-888).

14. The method according to claim 1, comprising the added step of administering to said subject after a time lapse an additional amount of a PARP-1 inhibitor or a composition comprising same for diminishing, suppressing or minimizing intentional or unintentional stimulus.

15. The method according to claim 14, wherein said PARP-1 inhibitor is administered to said subject prior, during or after intentional or unintentional exposure to a stimulus.

* * * * *